(12) United States Patent
Ishida et al.

(10) Patent No.: US 11,927,575 B2
(45) Date of Patent: Mar. 12, 2024

(54) CONTENT DETERMINATION ASSISTANCE SYSTEM AND CONTENT DETERMINATION ASSISTANCE METHOD

(71) Applicant: FRONTIER LABORATORIES LTD., Koriyama (JP)

(72) Inventors: Kazuko Ishida, Fukushima (JP); Atsushi Watanabe, Fukushima (JP); Chuichi Watanabe, Fukushima (JP)

(73) Assignee: FRONTIER LABORATORIES LTD., Koriyama (JP)

( * ) Notice: Subject to any disclaimer, the term of this patent is extended or adjusted under 35 U.S.C. 154(b) by 361 days.

(21) Appl. No.: 17/431,247

(22) PCT Filed: Feb. 21, 2020

(86) PCT No.: PCT/JP2020/007090
§ 371 (c)(1),
(2) Date: Aug. 16, 2021

(87) PCT Pub. No.: WO2021/005821
PCT Pub. Date: Jan. 14, 2021

(65) Prior Publication Data
US 2022/0137014 A1    May 5, 2022

(30) Foreign Application Priority Data

Jul. 10, 2019  (JP) ................ 2019-128260
Dec. 10, 2019  (JP) ................ 2019-223199

(51) Int. Cl.
*G01N 30/86*   (2006.01)
*G01N 27/62*   (2021.01)
*G01N 30/72*   (2006.01)

(52) U.S. Cl.
CPC ........ *G01N 30/8679* (2013.01); *G01N 27/62* (2013.01); *G01N 30/7206* (2013.01)

(58) Field of Classification Search
None
See application file for complete search history.

(56) References Cited

U.S. PATENT DOCUMENTS

| 2008/0208485 A1* | 8/2008 | Gorenstein | ......... H01J 49/0036 702/28 |
| 2009/0001261 A1* | 1/2009 | Yamaguchi | ........ G01N 30/8675 250/281 |

(Continued)

FOREIGN PATENT DOCUMENTS

| JP | 2000-035422 | 2/2000 |
| JP | 2005-091344 | 4/2005 |

(Continued)

OTHER PUBLICATIONS

International Search Report, dated Apr. 21, 2020, 3 pages.
(Continued)

*Primary Examiner* — Lina Cordero
(74) *Attorney, Agent, or Firm* — Rankin, Hill & Clark LLP

(57) ABSTRACT

There is provided a content determination assistance system capable of efficiently assisting in identifying a mixture that is highly likely to be contained in a sample. The content determination assistance system records characteristic mass spectrum data for each of known compounds. The content determination assistance system extracts the corresponding current-sample mass spectrum from the current-sample mass spectrum data, and detects a high intensity mass spectra from the corresponding current-sample mass spectrum. The content determination assistance system outputs a degree of concordance in the mass spectrum between a known compound subject to determination and a current sample using the characteristic mass spectrum and the high intensity mass spectrum.

5 Claims, 11 Drawing Sheets

(56) References Cited

U.S. PATENT DOCUMENTS

| | | | |
|---|---|---|---|
| 2014/0278146 A1 | 9/2014 | Sigman et al. | |
| 2018/0120327 A1* | 5/2018 | Marshall et al. | |
| 2019/0234916 A1* | 8/2019 | Yamamura | H01J 49/04 |
| 2020/0232956 A1* | 7/2020 | Kuehl | H01J 49/0036 |
| 2021/0098241 A1* | 4/2021 | Kuehl | G16B 40/00 |

FOREIGN PATENT DOCUMENTS

| | | |
|---|---|---|
| JP | 2011-033346 | 2/2011 |
| JP | 2011-209062 | 10/2011 |
| JP | 2016-061670 | 4/2016 |
| JP | 2017-096668 | 6/2017 |
| JP | 2019-074391 | 5/2019 |
| WO | 2017/077618 | 5/2017 |
| WO | 2018/138901 | 8/2018 |

OTHER PUBLICATIONS

European Search Report dated Jun. 5, 2023, European Application No. 20837083.3, English text, 6 pages.

Pyrolysis GC/MS and IR Spectroscopy in Chitin Analysis of Molluscan Shells, Takeshi Furuhashi et al., Published online: May 22, 2014, Bioschience, Biotechnology, and Biochemistry, English text, 12 pages.

\* cited by examiner

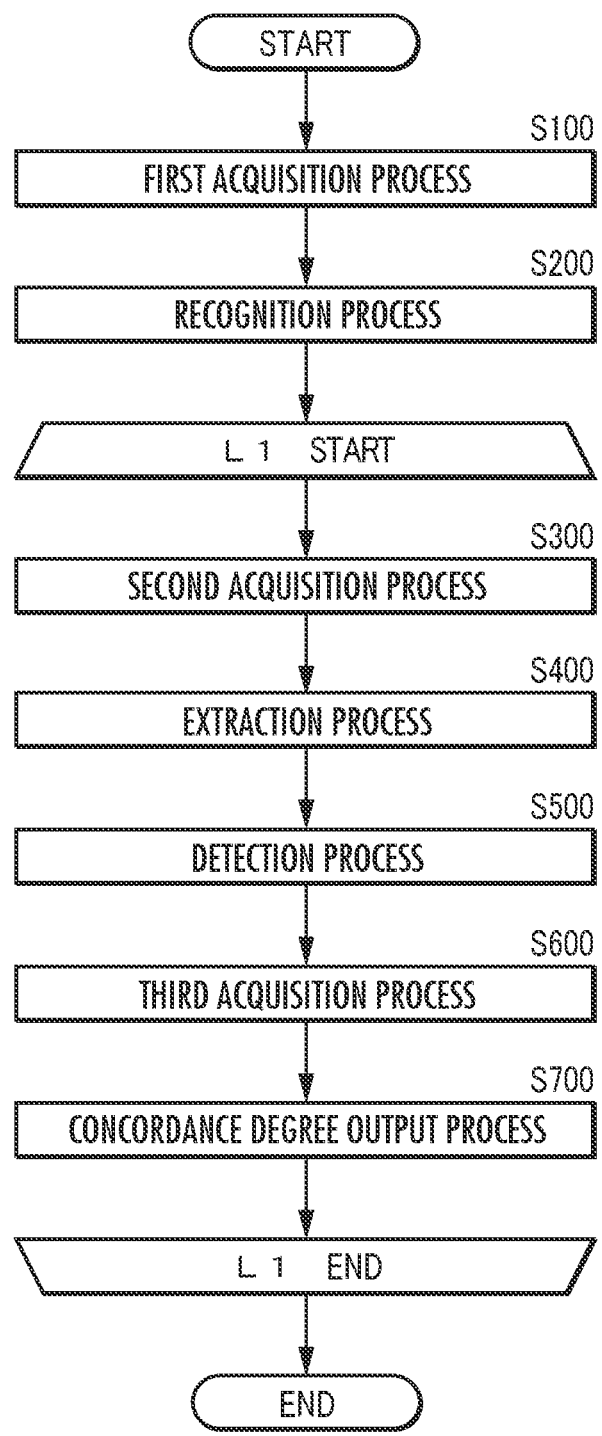

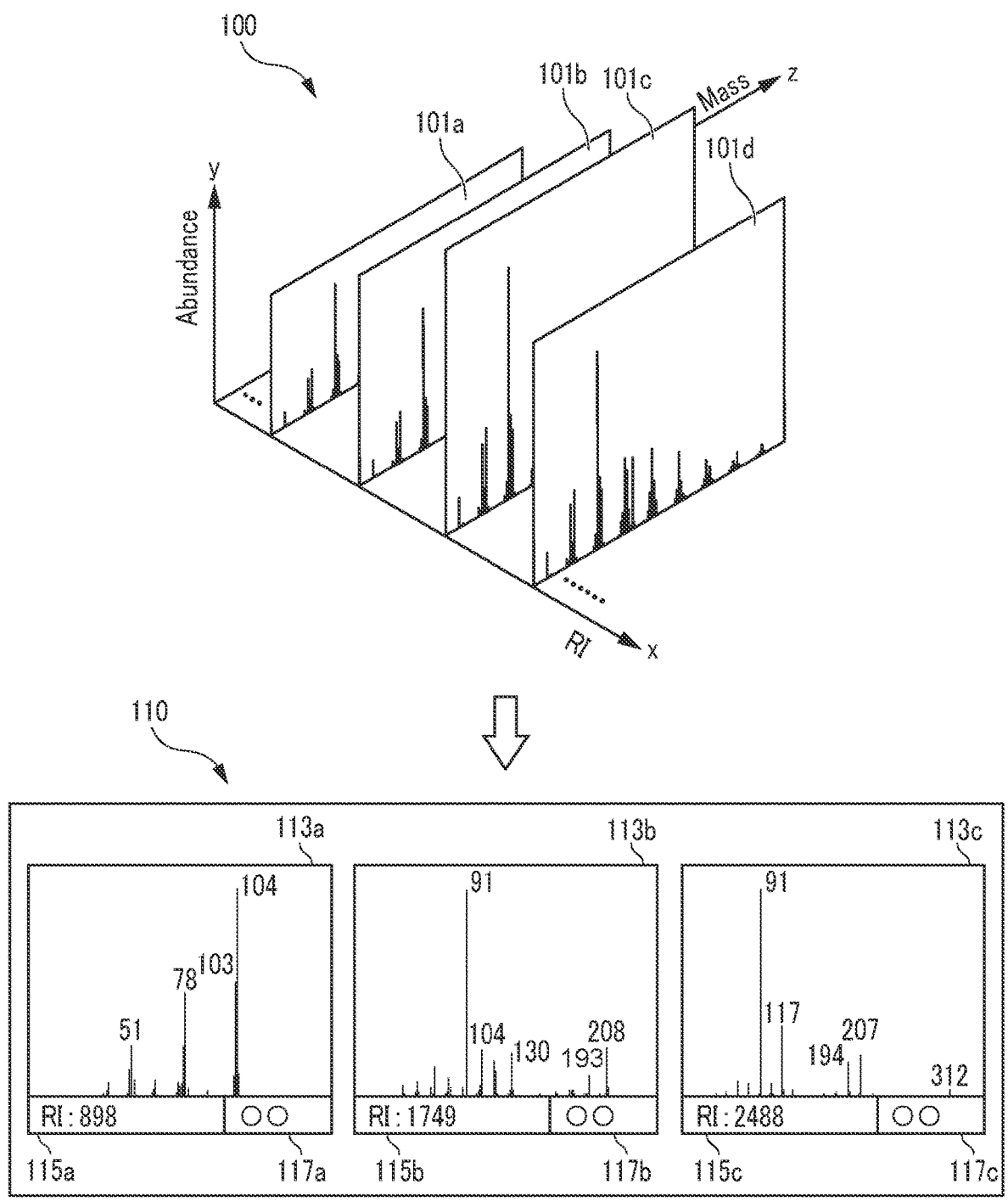

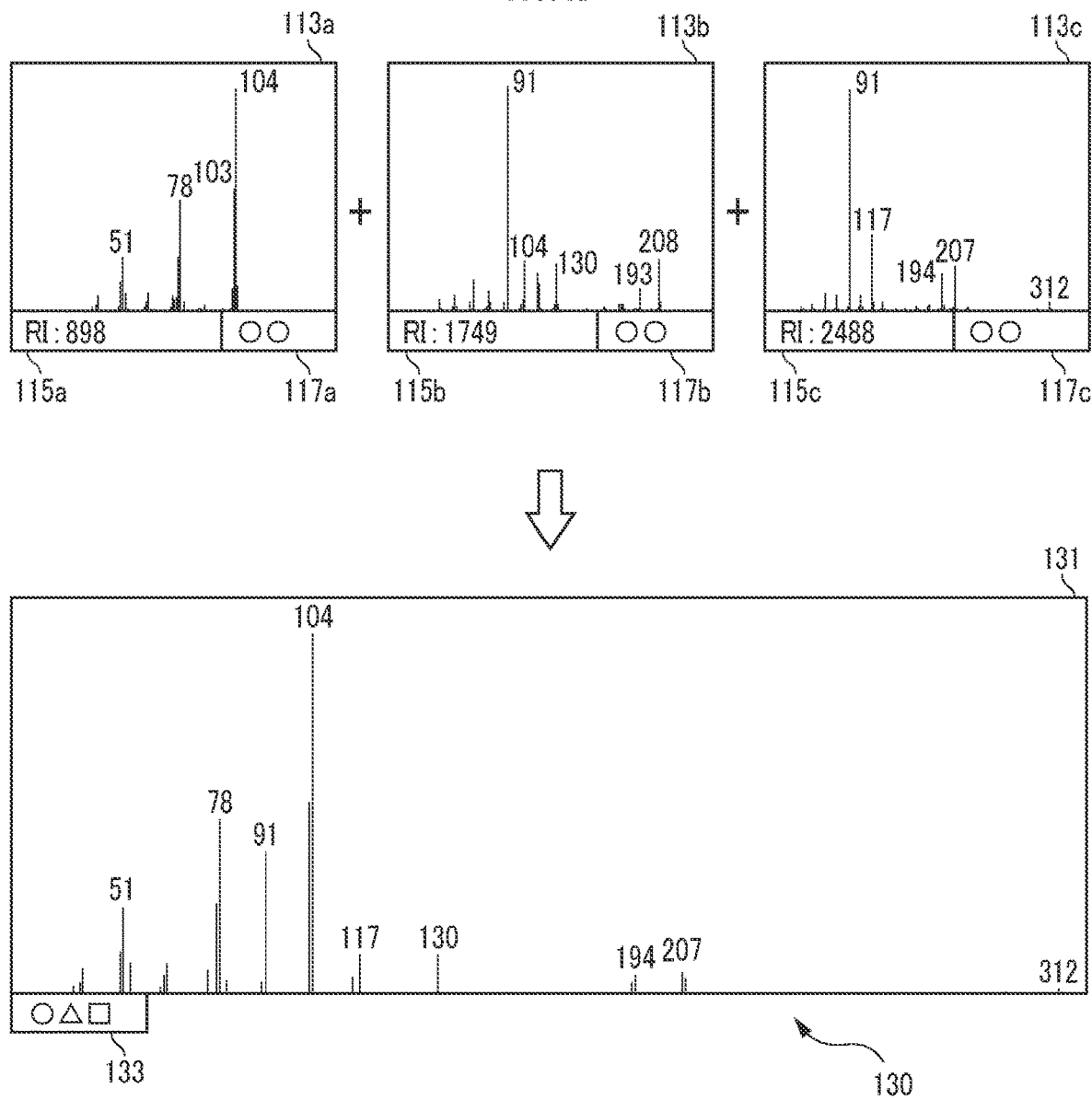

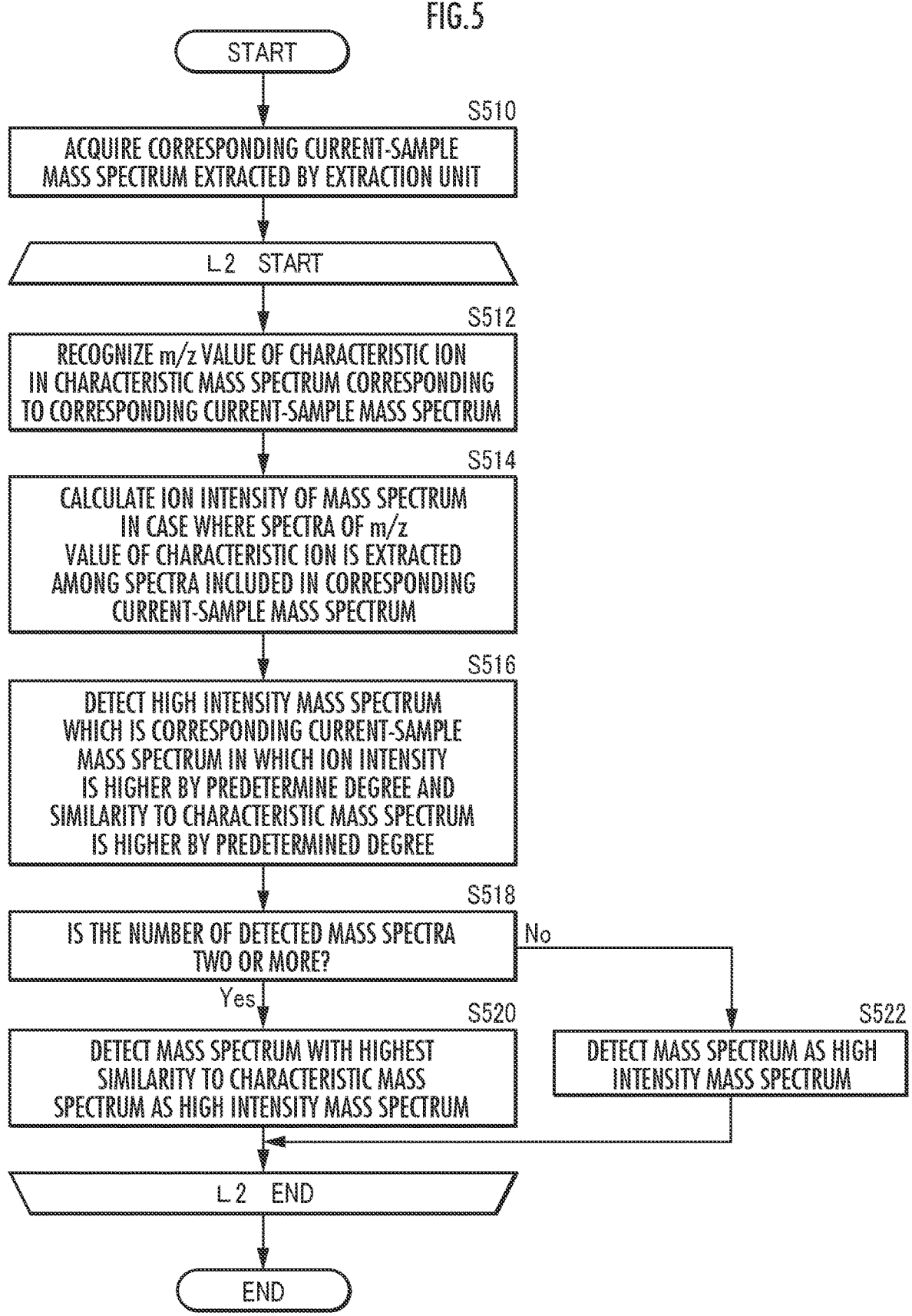

FIG.6
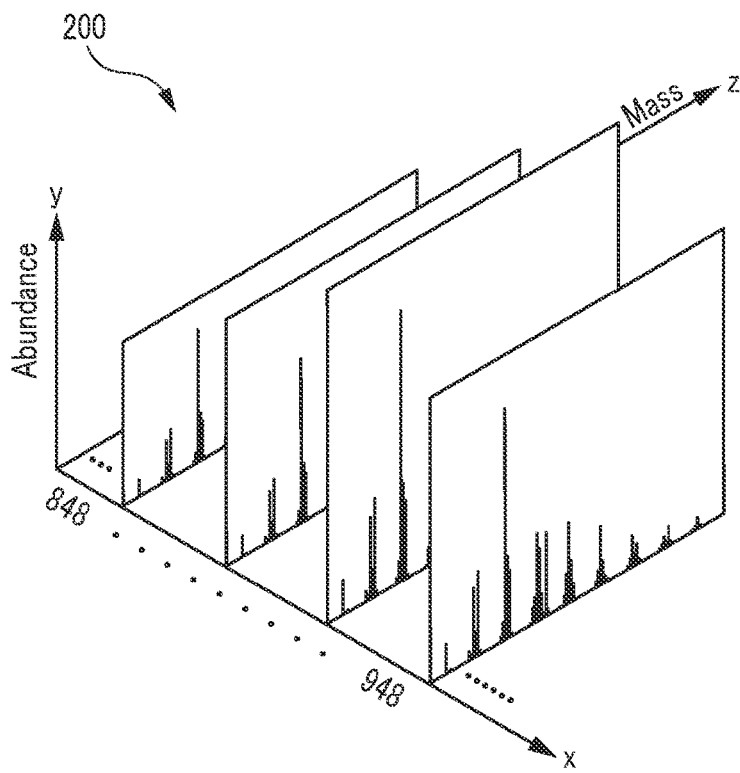
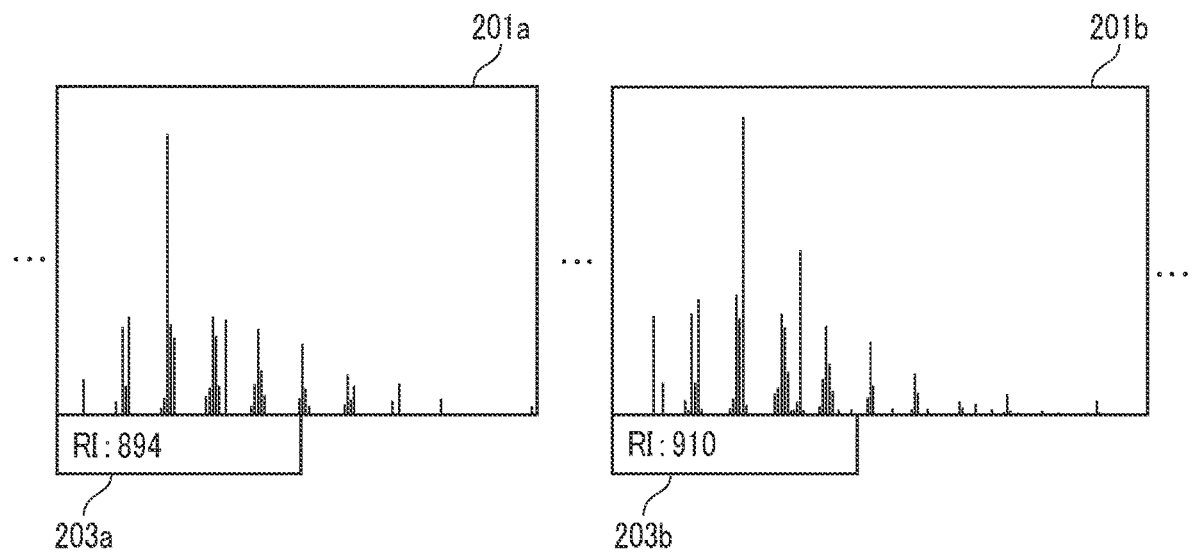

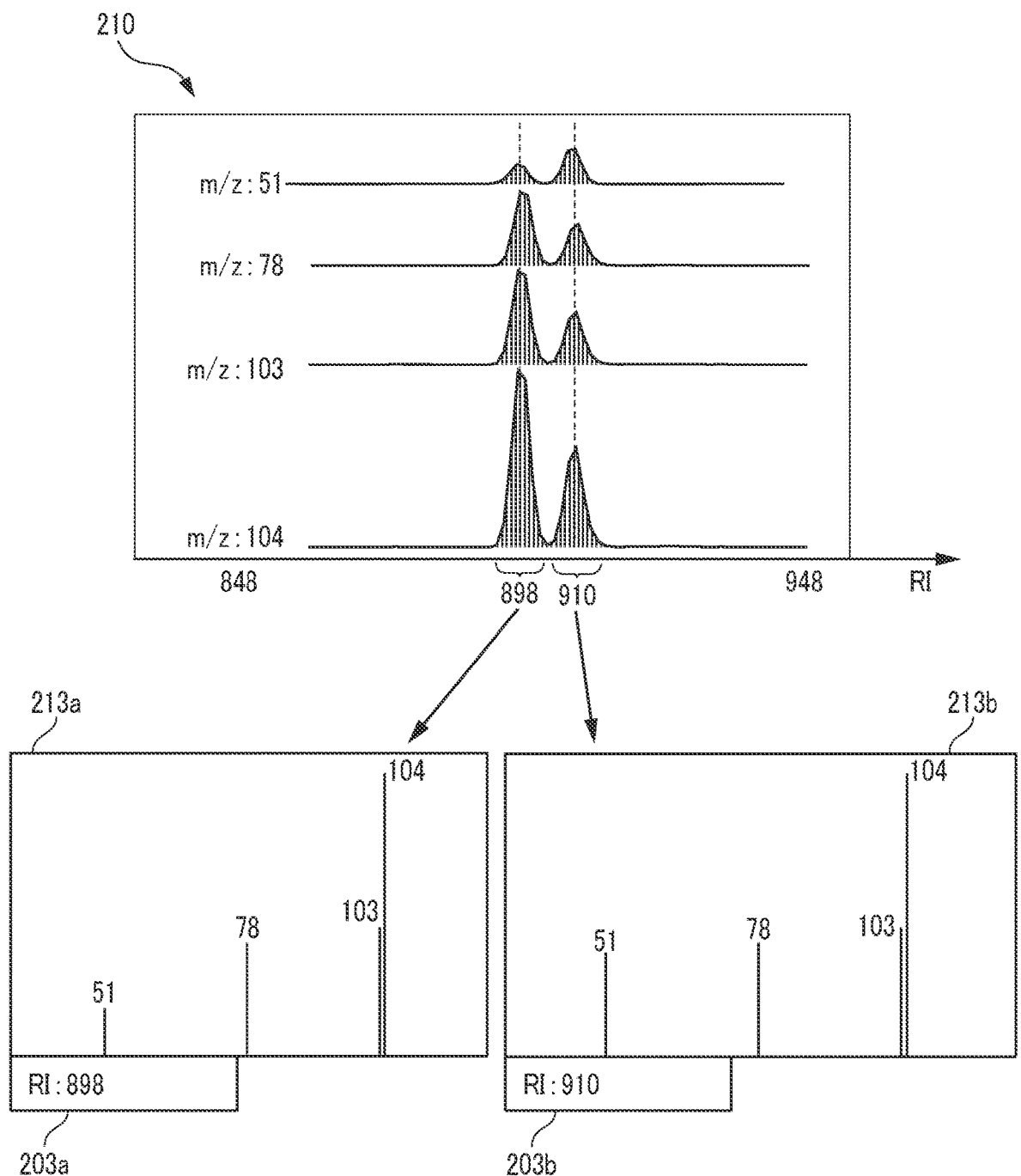

FIG.7B
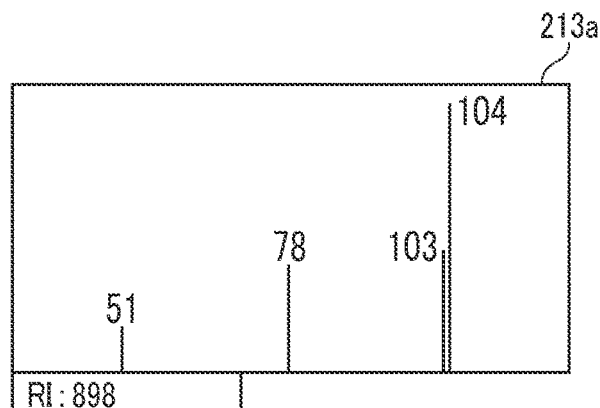
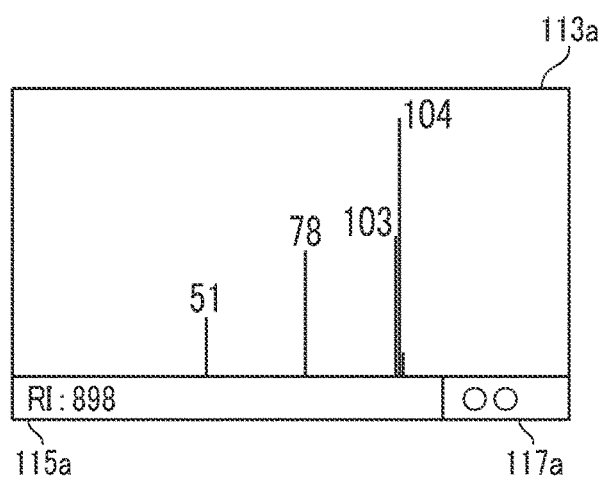
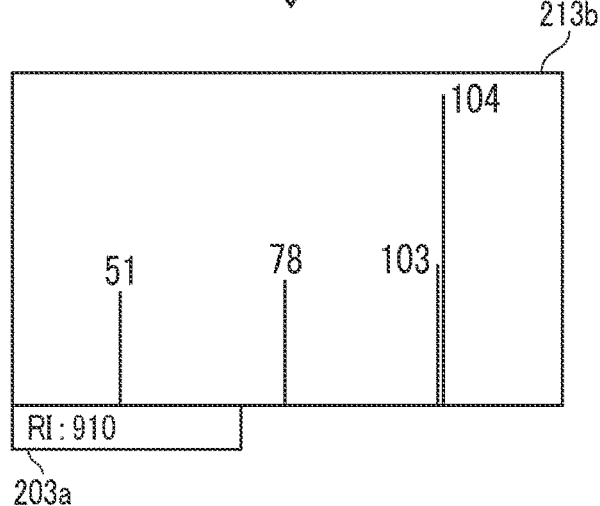

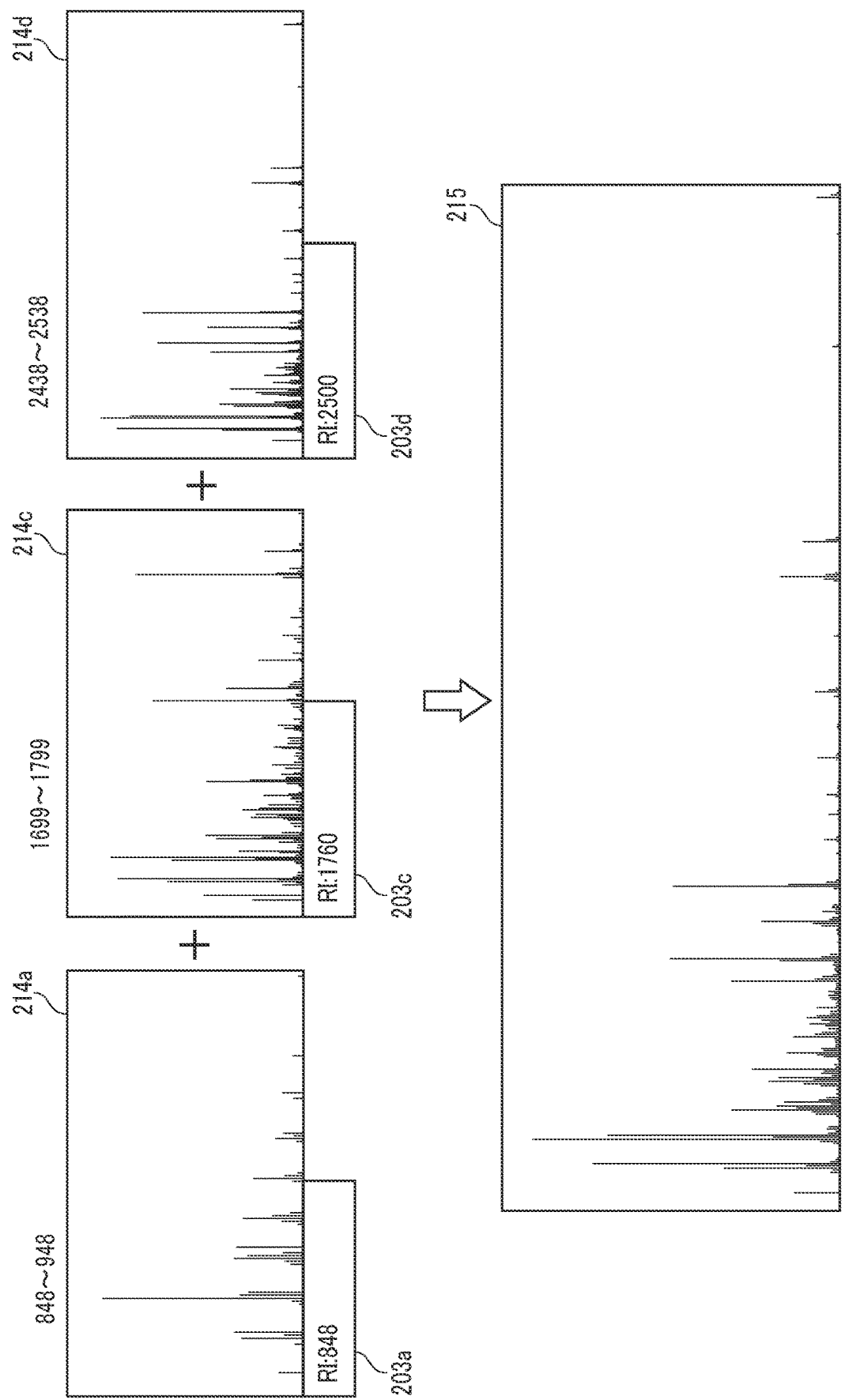

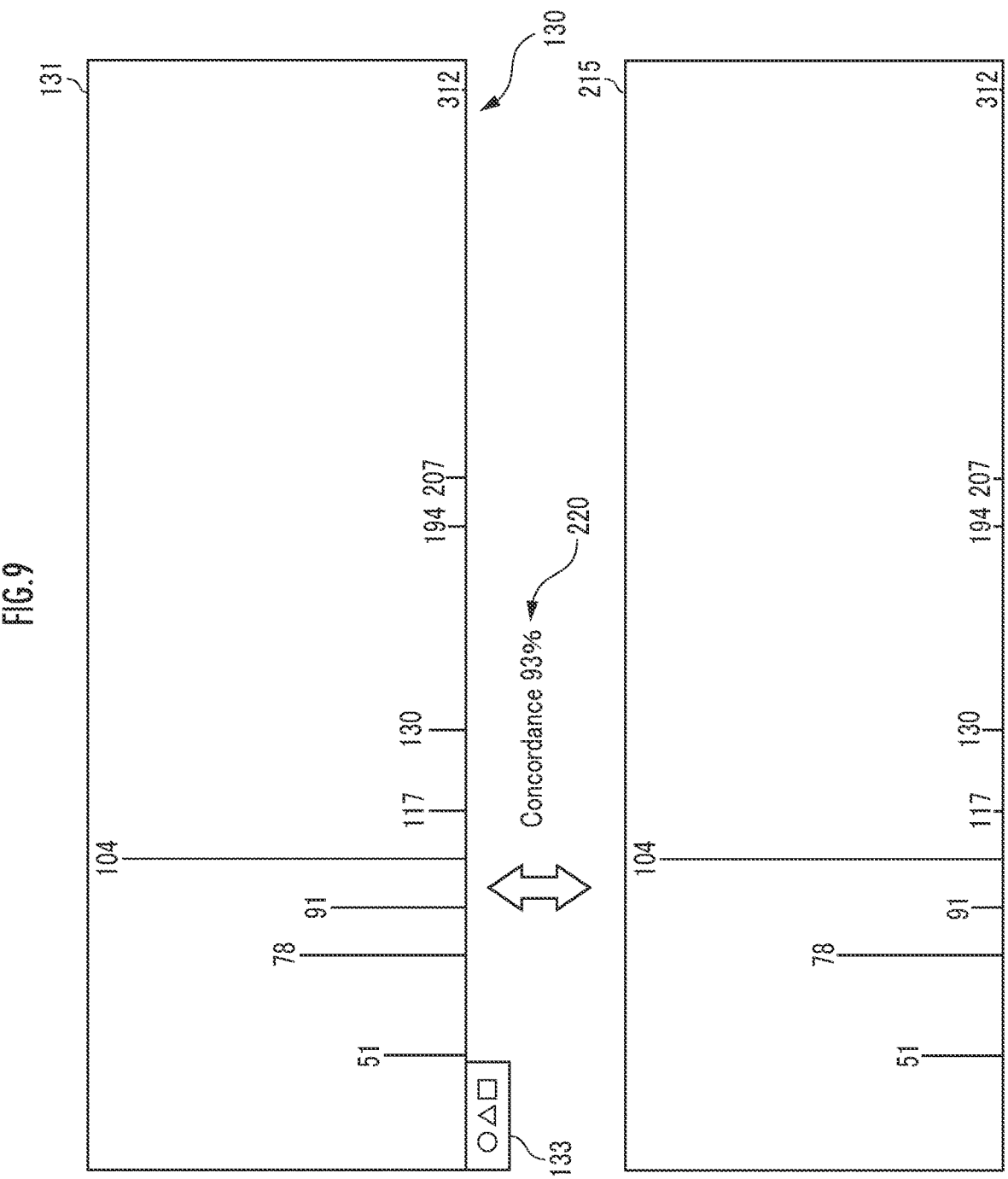

CONTENT DETERMINATION ASSISTANCE SYSTEM AND CONTENT DETERMINATION ASSISTANCE METHOD

TECHNICAL FIELD

The present invention relates to a content determination assistance system capable of assisting a user in determining whether a known compound is contained in a sample, and a content determination assistance method.

BACKGROUND ART

There has been conventionally known a search apparatus capable of identifying a sample of a compound (for example, Patent Literature 1).

According to a search apparatus of Patent Literature 1, a type of the compound can be identified from a chromatogram obtained from pyrolysis GC/MS analysis of a sample.

CITATION LIST

Patent Literature

Patent Literature 1: Japanese Patent Laid-Open No. 2000-35422

SUMMARY OF INVENTION

Technical Problem

The search apparatus of Patent Literature 1 identifies a compound contained in a sample based on a concordance ratio of a combined mass spectrum of the sample obtained by adding up detection data of each peak in a chromatogram obtained from the pyrolysis GC/MS analysis of the sample and a combined mass spectrum of a known sample obtained in the same manner.

As described above, the search apparatus of Patent Literature 1 is assumed to be capable of easily finding out a peak indicating the presence of a compound to be searched for from the peaks in a chromatogram obtained from the pyrolysis GC/MS analysis of the sample.

However, in the case where a variety of compounds other than a compound subject to determination whether to be contained in the sample are contained as contaminants, it is not easy to find a peak indicating the presence of the compound from peaks in the chromatogram obtained by the pyrolysis GC/MS analysis of the sample or it may be impossible to find out the peak. This is because many peaks indicating the presence of various compounds other than the compound subject to determination are detected, or the peak indicating the presence of the compound is relatively very small in magnitude, and consequently the peak of the compound is buried in the peaks of various compounds other than the compound.

For example, in a total ion chromatogram TIC1 shown in an upper portion of FIG. 1 obtained from the pyrolysis GC/MS analysis of a standard sample of a known compound subject to determination whether to be contained in a sample, peaks are detected at retention indices (RIs) of 898, 1749, and 2488. On the other hand, in a total ion chromatogram TIC2 shown in a lower portion of FIG. 1 obtained by the analysis of the sample in the same manner, for example, it is difficult to find out a peak around the RI of 898 because the peak is relatively small.

If a peak indicating the presence of a compound subject to determination cannot be found out from the total ion chromatogram, this means that the mass spectrum indicating the presence of the compound subject to determination is not included in a combined mass spectrum of a current sample even if the compound subject to determination is contained in the current sample. As a result, a concordance ratio of the combined mass spectrum of the current sample and the combined mass spectrum of the known sample becomes low.

Therefore, a user cannot determine the reason why the concordance ratio is so low: because the compound subject to determination is not contained in the current sample, or because the peak indicating the presence of the compound subject to determination is buried in peaks of the contaminants, and therefore cannot be found out.

In this way, in the case where a variety of compounds other than the compound subject to determination whether to be contained in the sample are contained as contaminants in the sample, it is difficult to determine whether the compound subject to determination is contained even if the search apparatus of Patent Literature 1 is used.

In view of such a problem of the conventional art, an object of the present invention is to provide a content determination assistance system capable of assisting a user in determining whether a known compound is contained in a sample even when a variety of compounds are contained in the sample as contaminants.

Solution to Problem

A content determination assistance system and a content determination assistance method according to the present invention are a system and a method which can assist a user in determining whether a known compound is contained in a sample by outputting a degree of concordance between a mass spectrum detected by separating a mixture of pyrolyzates obtained by pyrolyzing the known compound pre-recorded in the system into the pyrolyzates and subjecting the pyrolyzates to mass analysis (so-called "pyrolysis (GC/MS analysis," including "reactive pyrolysis GC/MS analysis"; the same applies hereinafter), and a mass spectrum detected by subjecting a current sample to the analysis in the same manner as an index indicating a level of possibility that a target known compound is contained in the current sample. The configuration is as follows.

A content determination assistance system according to the present invention which assists a user in determining whether a known compound is contained in a current sample comprises:

a recording unit configured to record, for each known compound, characteristic mass spectrum data which is information including a plurality of characteristic mass spectra which are characteristic mass spectra of a standard sample among mass spectra included in known-compound mass spectrum data which is time series data of the mass spectra at predetermined time intervals, the mass spectra being detected by the pyrolysis GC/MS analysis of a standard sample of the known compound, a characteristic retention time (RT) which is a time when each of the characteristic mass spectra is detected or a characteristic retention index (RI) obtained by indexing the time by a predetermined method, and m/z values of characteristic ions included in each of the characteristic mass spectra;

a first acquisition unit configured to acquire current-sample mass spectrum data which is information including time series data of the mass spectra of the current sample at the predetermined time intervals, the time series data being collected in the same manner as the known-compound mass spectrum data, and information obtained by indexing times when the respective mass spectra are detected or by indexing the times by the predetermined method;

a recognition unit configured to recognize a known compound subject to determination based on information for specifying the known compound subject to determination, the known compound subject to determination being subjected to determination whether to be contained in the current sample;

a second acquisition unit configured to acquire, from the recording unit, the m/z values of the respective characteristic ions and the characteristic RT or the characteristic RI, for each of the characteristic mass spectra relating to the recognized known compound subject to determination;

an extraction unit configured to extract, from the current-sample mass spectrum data, a plurality of corresponding current-sample mass spectra which are mass spectra detected in predetermined periods including RTs corresponding to the characteristic RTs or RIs corresponding to the characteristic RIs, respectively, based on the characteristic RTs or the characteristic RIs acquired by the second acquisition unit;

a detection unit configured to detect, from the plurality of corresponding current-sample mass spectra extracted by the extraction unit, a high intensity mass spectrum in each of the predetermined periods, the high intensity mass spectrum being the corresponding current-sample mass spectrum in which ion intensity in the mass spectra forming a peak included in a mass chromatogram is higher by a predetermined degree, in a case where the mass chromatogram is drawn based on the mass spectra extracting the spectra of the m/z values of the characteristic ions acquired by the second acquisition unit among the spectra included in each corresponding current-sample mass spectrum, and a similarity to the characteristic mass spectrum corresponding to the corresponding current-sample mass spectrum is higher by a predetermined degree; and a concordance degree output unit configured to output a degree of concordance between the mass spectra of the known compound subject to determination and the mass spectra of the current sample using the plurality of characteristic mass spectra relating to the known compound subject to determination and the high-intensity mass spectra detected by the detection process in the respective predetermined periods.

According to the present invention, the recording unit records, for each known compound, characteristic mass spectrum data which is information including a plurality of characteristic mass spectra which are characteristic mass spectra of a standard sample, a characteristic retention time go which is a time when each of the characteristic mass spectra is detected or a characteristic retention index (RI) obtained by indexing the time by a predetermined method, and m/z values of characteristic ions included in each of the characteristic mass spectra, among mass spectra included in known-compound mass spectrum data which is time series data of the mass spectra at predetermined time intervals, the mass spectra being detected by the pyrolysis GC/MS analysis of a standard sample of the known compound.

A large number of compounds are obtained as pyrolyzates of original known compound when the standard sample of the known compound is pyrolyzed at a predetermined high temperature of about 600° C. (in the case of reactive pyrolysis GC/MS analysis, for example, about 350° C. to 400° C.), for example, using a pyrolyzer. The large number of compounds obtained as pyrolyzates contain the plurality of characteristic compounds which are obtained when the standard sample of the known compound is pyrolyzed.

When the large number of compounds thus obtained are separated by a separation column, for example, each separated compound is ionized and detected by a mass spectrometer at predetermined intervals and the m/z value and ion intensity of each ion are measured (pyrolysis GC/MS analysis), the information indicating the time when each compound is detected and the mass spectrum corresponding to each compound are obtained.

In the present invention, the recording unit records, as the characteristic mass spectrum of the known compound, each of a plurality of characteristic compound mass spectra obtained by separating a mixture of pyrolyzates obtained by pyrolyzing the standard sample of the known compound into the pyrolyzates and subjecting the pyrolyzates to mass analysis, so-called pyrolysis GC/MS analysis, the plurality of characteristic compound mass spectra being extracted from the mass spectra thus obtained.

The information of the m/z value and ion intensity of each ion is included in each mass spectrum. However, a plurality of ions characteristic of the mass spectrum are included in these ions.

In the present invention, the m/z values of the characteristic ions included in each characteristic mass spectrum are stored in the recording unit as a part of the characteristic mass spectrum data.

The first acquisition unit acquires current-sample mass spectrum data which is information including time series data of the mass spectra of the current sample at the predetermined time intervals, the time series data being collected in the same manner as the known-compound mass spectrum data, and information obtained by indexing times when the respective mass spectra are detected or by indexing the times by the predetermined method.

A slight difference may occur between an RT or RI of the characteristic mass spectrum corresponding to a pyrolyzate and an RT or RI of the mass spectrum of the current sample corresponding to the same pyrolyzate.

According to the present invention, the recognition unit recognizes a known compound subject to determination based on information for specifying the known compound subject to determination, the known compound subject to determination being the known compound to be subjected to determination whether to be contained in the current sample, and the second acquisition unit acquires, from the recording unit, the m/z values of the respective characteristic ions and the characteristic RT or the characteristic RI, for each of the characteristic mass spectra relating to the recognized known compound subject to determination.

The extraction unit extracts, from the current-sample mass spectrum data, a plurality of corresponding current-sample mass spectra which are mass spectra acquired in predetermined periods including RTs corresponding to the characteristic RTs or RIs corresponding to the characteristic RIs, respectively, based on the characteristic RTs or the characteristic RIs acquired by the second acquisition unit.

In this way, the mass spectra acquired in a period having a predetermined width can be extracted from the current-sample mass spectrum data, as the corresponding current-sample mass spectra, with the RT corresponding to the characteristic RT or the RI corresponding to the characteristic RI as reference, thereby enhancing the reliability with which the mass spectra corresponding to the characteristic mass spectra are extracted from the current-sample mass spectrum data, as the corresponding current-sample mass spectra, even when a slight difference occurs between the RT or RI of the characteristic mass spectrum corresponding to a pyrolyzate and the RT or RI of the mass spectrum of the current sample corresponding to the same pyrolyzate.

The detection unit detects, from the plurality of corresponding current-sample mass spectra, a high intensity mass spectrum in each of the predetermined periods, the high intensity mass spectrum being the corresponding current-sample mass spectrum in which ion intensities in the mass spectra forming peaks included in a mass chromatogram are higher by a predetermined degree, in a case where the mass chromatogram is drawn based on the mass spectra extracting the spectra of the m/z values of the characteristic ions acquired by the second acquisition unit among the spectra included in each corresponding current-sample mass spectrum, and a similarity to the characteristic mass spectrum corresponding to the corresponding current-sample mass spectrum is higher by a predetermined degree.

In this way, the high intensity mass spectrum can be selectively extracted from the corresponding current-sample mass spectra by focusing not on the total ion intensity but on individual characteristic ions of the known compound subject to determination, thereby enhancing the reliability with which the high intensity mass spectrum having high similarity to the characteristic mass spectrum indicating the presence of each characteristic pyrolyzate obtained by pyrolyzing the compound subject to determination is detected in each of the predetermined periods, even when a variety of compounds other than the compounds subject to determination whether to be contained in the current sample are contained as contaminants.

The concordance degree output unit outputs a degree of concordance between the mass spectra of the known compound subject to determination and the mass spectra of the current sample using the plurality of characteristic mass spectra relating to the known compound subject to determination and the high-intensity mass spectra detected by the detection unit in the respective predetermined periods.

In this way, a level of possibility that the known compound subject to determination is contained in the current sample is output as the degree of concordance. Therefore, the user can be intuitively informed that the level of possibility that the known compound subject to determination is contained in the current sample, which makes it possible to effectively assist the user in determining whether the compound subject to determination is contained in the current sample.

Thus, the content determination assistance system of the present invention can efficiently assist a user in determining whether a known compound is contained in a sample even when a variety of compounds other than the compound subject to determination whether to be contained in the sample are contained as contaminants.

In the content determination assistance system according to the present invention, it is preferable that
the recording unit records, for each known compound, combined known-sample mass spectrum data which is information including combined known-sample mass spectra which are mass spectra obtained by combining, for each of ions of the same m/z value, the plurality of characteristic mass spectra, a third acquisition unit is provided to acquire combined current-sample mass spectrum which are mass spectra obtained by combining, for each of ions of the same m/z value, the high intensity mass spectra detected by the detection unit in the respective predetermined periods, and the concordance degree output unit is configured to output, as a degree of concordance, a degree of concordance between the combined known-sample mass spectra relating to the known compound subject to determination and the combined current-sample mass spectra.

Even when it has been found that the high intensity mass spectrum having high similarity to the characteristic mass spectrum indicating the presence of each characteristic pyrolyzate obtained by pyrolyzing the compound subject to determination is detected in each of the predetermined periods, the compound subject to determination is not necessarily contained in the current sample.

This is because, for example, some of the pyrolyzates obtained by pyrolyzing the plurality of compounds other than the compound subject to determination which is contained in the sample are combined, which may rarely cause coincidence with all of the characteristic pyrolyzates obtained by pyrolyzing the compound subject to determination.

However, even when only the coincidence with the characteristic pyrolyzates happens, the coincidence with the balance in the quantities of the characteristic pyrolyzates is very rare. Accordingly, it is preferable that a level of possibility that the known compound subject to determination is contained in the current sample is output in view of whether the coincidence in the balance in the quantities of the characteristic pyrolyzates happens.

In the present invention, the recording unit records, for each known compound, combined known-sample mass spectrum data which is information including combined known-sample mass spectra which are mass spectra obtained by combining, for each of ions of the same m/z value, the plurality of characteristic mass spectra obtained via the above-described processes.

Additionally, the third acquisition unit acquires combined current-sample mass spectra which are mass spectra obtained by combining, for each of ions of the same m/z value, the high intensity mass spectra detected by the detection unit in the respective predetermined periods.

The combined known-sample mass spectrum is information obtained by combining, for the same m/z value, the characteristic mass spectra. The combined current-sample mass spectrum is information obtained by combining, for the same m/z value, the high intensity mass spectra. In the combined known-sample mass spectrum and the combined current-sample mass spectrum, the ion intensities in the mass spectrum corresponding to a pyrolyzate which is obtained in a larger quantity when the sample is pyrolyzed are high, and the ion intensities in the mass spectrum corresponding to a pyrolyzate which is obtained in a smaller quantity when the sample is pyrolyzed are low.

The information about the balance in the quantities of the characteristic pyrolyzates is included in both of the combined known-sample mass spectra and the combined current-sample mass spectra.

Then, the concordance degree output unit outputs, as the degree of concordance, a degree of concordance between the combined known-sample mass spectra relating to the known compound subject to determination and the combined current-sample mass spectra.

In this way, the level of possibility that the known compound subject to determination is contained in the current sample is output as the degree of concordance in view of not only the presence or absence of the individual high intensity mass spectra but also the degree of coincidence in the balance in the quantities of the pyrolyzates between the standard sample and the current sample. Therefore, the reliability of the output result can be enhanced, which makes it possible to effectively assist the user in determining whether the known compound is contained in the current sample.

Thus, the content determination assistance system of the present invention can efficiently assist a user in high reliable determination as to whether a known compound is contained in a sample even when a variety of compounds other than the compound subject to determination whether to be contained in the sample are contained as contaminants.

In the content determination assistance system according to the present invention,
- it is preferable that the detection unit acquires the similarity only using the spectra of the m/z values of the characteristic ions.

According to the present invention, the similarity is acquired only using the spectra of the m/z values of the characteristic ions, when the similarity between each of the high intensity mass spectra and the characteristic mass spectrum corresponding to the high intensity mass spectrum is acquired by the detection unit.

In this way, a process of outputting the similarity between each of the high intensity mass spectra and the characteristic mass spectrum is performed, focusing on the characteristic ions, whereby the similarity can be efficiently output by the detection unit.

Thus, the content determination assistance system of the present invention can effectively and efficiently assist a user in determining whether a known compound is contained in a sample even when a variety of compounds other than the compound subject to determination whether to be contained in the sample are contained as contaminants.

In the content determination assistance system according to the present invention,
- it is preferable that
  the combined known-sample mass spectrum data includes m/z values of combined characteristic ions which are characteristic ions included in the combined known-sample mass spectrum, and
  the concordance degree output unit acquires and outputs the degree of concordance only using spectra of the m/z values of the combined characteristic ions.

According to the present invention, the combined known-sample mass spectrum data includes m/z values of combined characteristic ions which are characteristic ions included in the combined known-sample mass spectrum, and the concordance degree output unit acquires and outputs the degree of concordance only using spectra of the m/z, values of the combined characteristic ions.

In this way, a process of outputting the degree of concordance between the combined known-sample mass spectrum and the combined current-sample mass spectrum is performed, focusing on the combined characteristic ions, whereby the degree of concordance can be efficiently output by the concordance degree output unit.

Thus, the content determination assistance system of the present invention can effectively and efficiently assist a user in determining whether a known compound is contained in a sample even when a variety of compounds other than the compound subject to determination whether to be contained in the sample are contained as contaminants.

BRIEF DESCRIPTION OF DRAWINGS

FIG. 3 is a flowchart illustrating an example of processes of the entire content determination assistance system of the present embodiment.

FIG. 4A is a conceptual diagram illustrating contents of a characteristic mass spectrum in the content determination assistance system of the present embodiment.

FIG. 4B is a conceptual diagram illustrating contents of a combined known-sample mass spectrum in the content determination assistance system of the present embodiment.

FIG. 5 is a flowchart illustrating an example of a detection process of the content determination assistance system of the present embodiment.

FIG. 6 is a conceptual diagram illustrating contents of a corresponding current-sample mass spectrum in the content determination assistance system of the present embodiment.

FIG. 7A is a conceptual diagram illustrating contents of processes it e content determination assistance system of the present embodiment.

FIG. 7B is a conceptual diagram illustrating contents of processes in the content determination assistance system of the present embodiment.

FIG. 8 is a conceptual diagram illustrating contents of a combined current-sample mass spectrum in the content determination assistance system of the present embodiment.

FIG. 9 is a conceptual diagram illustrating a method of outputting a concordance degree in the content determination assistance system of the present embodiment.

DESCRIPTION OF EMBODIMENTS

Figure 1:
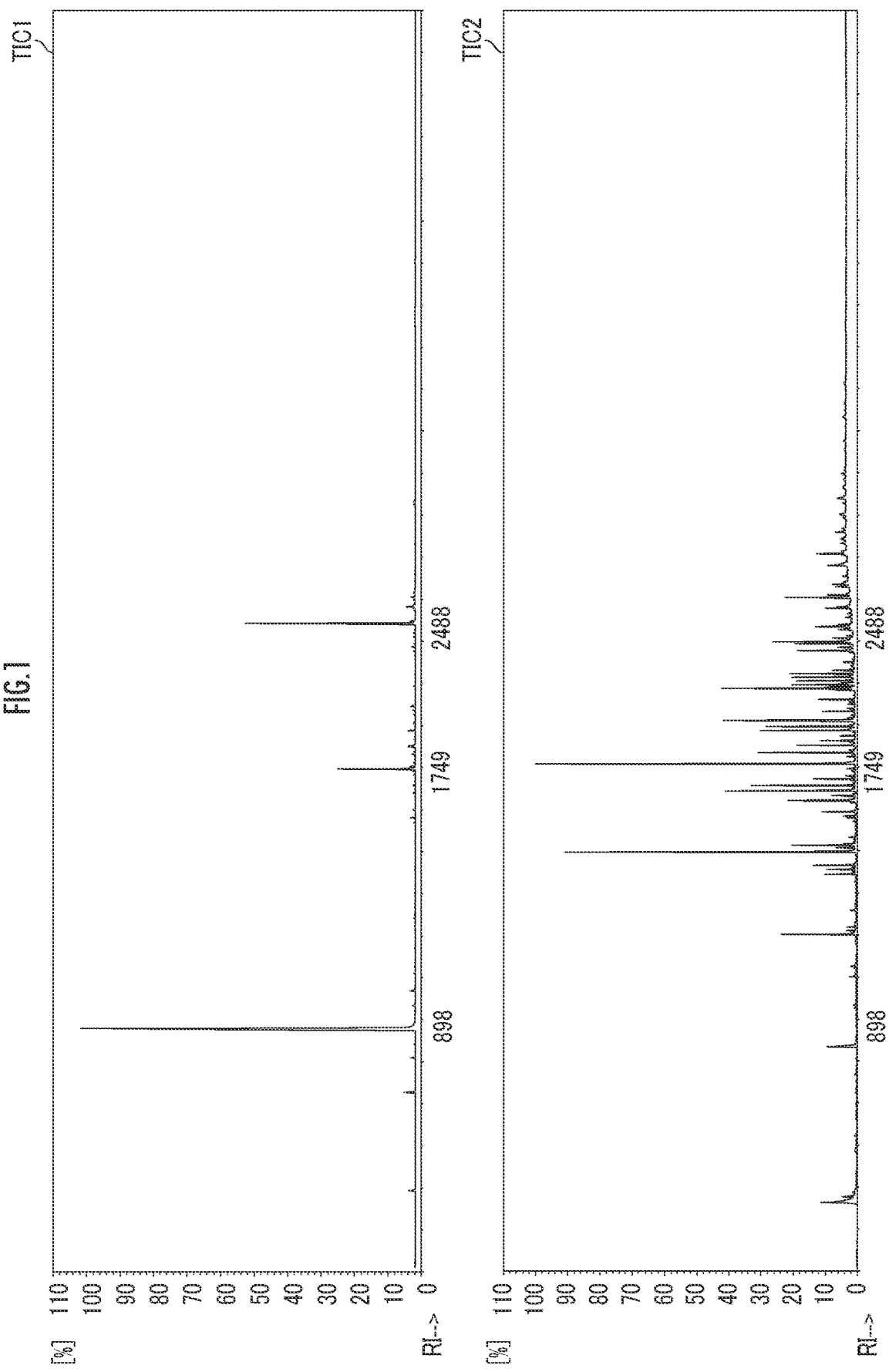
FIG. 1 includes charts showing total ion chromatograms of a known compound used in a conventional art and a current sample.
Figure 2:
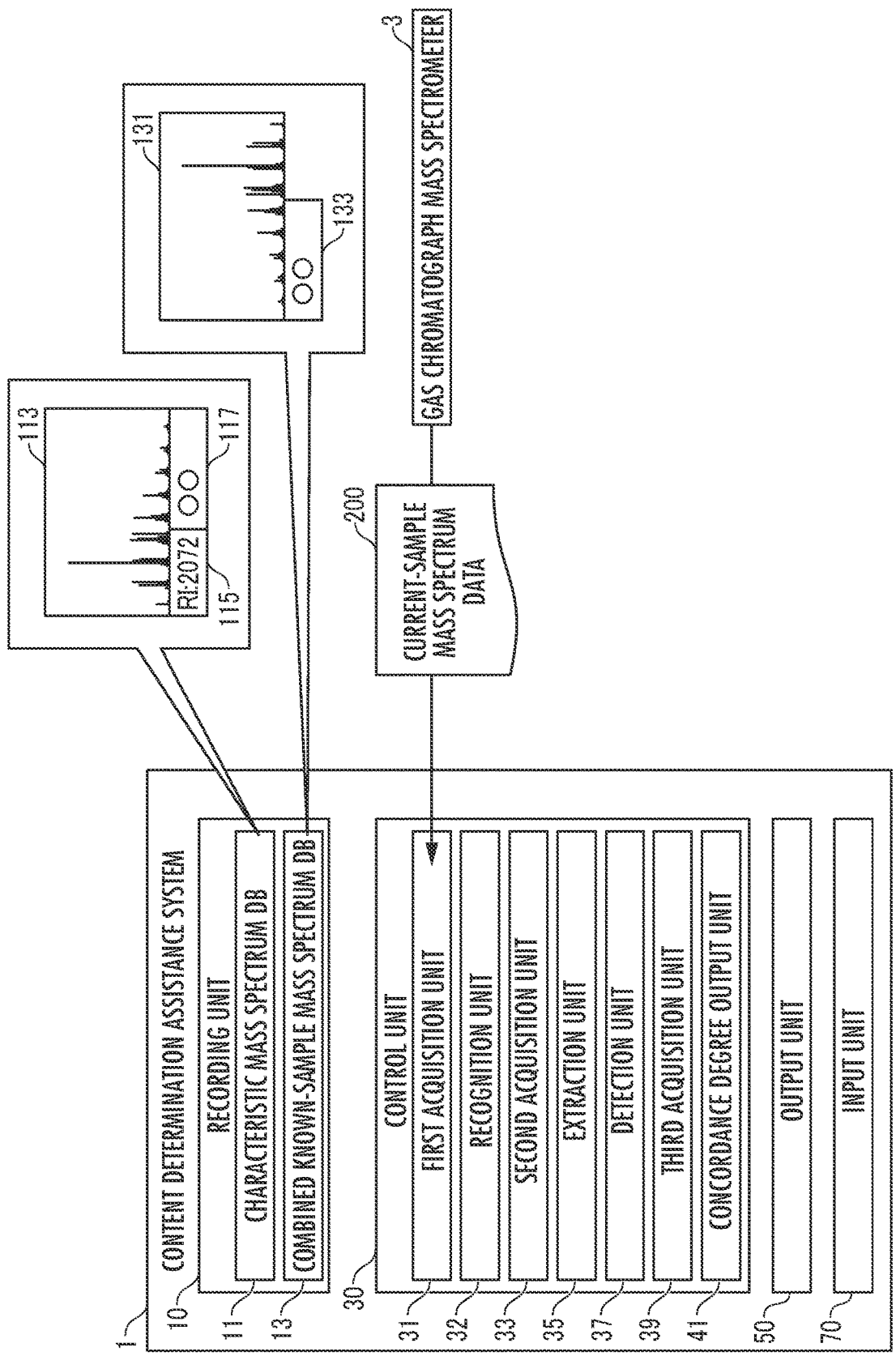
FIG. 2 is a configuration diagram illustrating an example of the entire configuration of a content determination assistance system of the present embodiment.

Hereinafter, embodiments of the present invention will be described using the drawings. Although in the following description, an embodiment in which content determination is assisted by using an RI of a mass spectrum will be described, the content determination may be performed by using an RT of the mass spectrum instead of the RI of the mass spectrum. As illustrated in 2, a content determination assistance system 1 of the present embodiment is a computer comprising a recording unit 10, a control unit 30, an output unit 50, and an input unit 70.

The recording unit 10 includes a storage device such as a read only memory (ROM), a random access memory (RAM), or a hard disk drive (HDD), and stores a characteristic mass spectrum database (DB) 11, a combined known-sample mass spectrum DB 13, and process results of the control unit 30.

The characteristic mass spectrum DB 11 stores, for each known compound, characteristic mass spectrum data 110 which is information including a plurality of characteristic mass spectra 113, a characteristic RI 115 of each of the characteristic mass spectra 113, and m/z values of characteristic ions included in each of the characteristic mass spectra 113.

The characteristic ion is, for example, an ion with higher ion intensity than other ions in each characteristic mass spectrum 113. Alternatively, for example, the characteristic ion may be also an ion which is not included in the other characteristic mass spectra 113 or an ion with low possibility of being included in the other characteristic mass spectra 113.

The characteristic mass spectrum 113 is a characteristic mass spectrum among mass spectra included in known-compound mass spectrum data 100 which is time series data of the mass spectra at predetermined time intervals, the mass spectra being detected by the pyrolysis GC/MS analysis of a standard sample of a known compound.

The characteristic mass spectrum is, for example, a mass spectrum of a pyrolyzate which is obtained in a larger quantity when the standard sample of the known compound is pyrolyzed, as compared when the other compounds are pyrolyzed. Alternatively, for example, the characteristic mass spectrum may be a mass spectrum showing a peak higher than the other peaks when a total ion chromatogram is drawn by using the known-compound mass spectrum data 100.

The characteristic RI 115 is information obtained by indexing, by a predetermined method, a time when each of the characteristic mass spectra 113 is detected.

The characteristic mass spectrum data 110 may further include information 117 indicating a name of the known compound corresponding to each characteristic mass spectrum 113.

The combined known-sample mass spectrum DB 13 stores, for each known compound, combined known-sample mass spectrum data 130.

The combined known-sample mass spectrum data 130 is information including combined known-sample mass spectra 131 which are mass spectra obtained by combining, for each of ions of the same m/z value, the characteristic mass spectra 113. The combined known-sample mass spectrum data 130 may further include information 133 indicating a name of the known sample corresponding to each combined known-sample mass spectrum 131, and m/z values of combined characteristic ions being the characteristic ions included in the combined known-sample mass spectra 131.

The combined characteristic ion is, for example, an ion with higher ion intensity than other ions in each combined known-sample mass spectrum 131. Alternatively, for example, the combined characteristic ion may be also an ion which is not included in the other combined known-sample mass spectra 131 or ions with low possibility of being included in the other combined known-sample mass spectra 131.

Even if the standard samples of known compounds of the same name are subjected to the pyrolysis GC/MS analysis to detect the characteristic mass spectrum data 110 and the combined known-sample mass spectrum data 130 based on the above-described characteristic mass spectrum data 110, the characteristic mass spectrum data 110 and the combined known-sample mass spectrum data 130 which are obtained under a different condition of measurement temperature (for example, the measurement is made at 400° C., 600° C. and the like), source (for example, the standard samples are obtained from company A, company B, and the like), or the like may be recorded in the recording unit 10 as those relating to the standard sample of another known compound.

In known-compound mass spectrum 101, the characteristic mass spectrum 113, and the combined known-sample mass spectrum 131, values indicating one or more m/z values at which respective peaks included in the mass spectrum are detected and a value indicating the ion intensity of each peak are included.

The control unit 30 includes an arithmetic processing unit such as a central processing unit (CPU), a memory, and an input/output (I/O) device. The control unit 30 may include a single processor or may include multiple processors which can communicate with one another.

The control unit 30 reads and executes a predetermined program to thereby function as a first acquisition unit 31, a recognition unit 32, a second acquisition unit 33, an extraction unit 35, a detection unit 37, a third acquisition unit 39, and a concordance degree output unit 41 which execute an arithmetic process described later.

The first acquisition unit 31 acquires current-sample mass spectrum data 200.

The content determination assistance system 1 and a gas chromatograph mass spectrometer (GC/MS) 3 are communicably connected to each other using a wired or wireless network, for example. The network is, for example, a local area network (LAN), a wide area network (WAN), or an internet communication network. The first acquisition unit 31 acquires the current-sample mass spectrum data 200 from the GC/MS 3 through the network in response to a user's operation or automatically.

The current-sample mass spectrum data 200 is information including time series data of the mass spectra of the current sample at predetermined time intervals, the time series data being collected in the same manner as the known-compound mass spectrum data, and information (RIs) obtained by indexing times when the respective mass spectra are detected, by the same method as the method used when times when the respective characteristic mass spectra 113 are detected are indexed. In the mass spectrum, values indicating one or more m/z values at which the respective peaks included in the mass spectrum are detected and a value indicating the ion intensity of each peak are included.

The recognition unit 32 recognizes a known compound subject to determination based on the information for specifying a known compound subject to determination, which is the above-described known compound subjected to determination whether to be contained in the current sample.

The second acquisition unit 33 acquires, from the recording unit 10, the m/z values of the respective characteristic ions and the characteristic RI 115, for each of the characteristic mass spectra 113 relating to the known compound subject to determination which is recognized by the recognition unit 32.

The extraction unit 35 extracts, from the current-sample mass spectrum data 200, a plurality of corresponding current-sample mass spectra 201 which are mass spectra detected in predetermined periods including RIs corresponding to characteristic RIs 115, respectively, based on the characteristic RIs 115 acquired by the second acquisition unit 33.

The detection unit 37 detects, from the plurality of corresponding current-sample mass spectra 201 extracted by the extraction unit 35, a high intensity mass spectrum 214 in each of the predetermined periods, the high intensity mass spectrum 214 being the corresponding current-sample mass spectrum 201 in which the ion intensities in the mass spectra forming peaks included in a mass chromatogram are higher by a predetermined degree, in the case where the mass chromatogram is drawn based on the mass spectra extracting the spectra of the m/z values of the characteristic ions acquired by the second acquisition unit 33 among the spectra included in each corresponding current-sample mass spectrum 201, and the similarity to the characteristic mass spectrum 113 corresponding to the corresponding current-sample mass spectrum is higher by a predetermined degree.

Additionally, the detection unit 37 may be configured to acquire the similarity only using the spectra of the m/z values of the characteristic ions.

The third acquisition unit 39 combines, for each of ions of the same m/z value, the high intensity mass spectra 214 detected by the detection unit 37 in the respective predetermined periods, and acquires mass spectra after the combination as combined current-sample mass spectra 215.

The concordance degree output unit 41 outputs a degree of concordance between the mass spectra of the known compound subject to determination and the mass spectra of the current sample using the plurality of characteristic mass spectra 113 relating to the known compound subject to determination and the high-intensity mass spectra 214 detected by the detection unit 37 in the respective predetermined periods.

More specifically, the concordance degree output unit 41 outputs the degree of concordance between the combined known-sample mass spectra 131 relating to the known compound subject to determination and the combined current-sample mass spectra 215.

The concordance degree output unit 41 may be configured to acquire and output, as the degree of concordance, a degree of concordance between the combined known-sample mass spectra 131 relating to the known compound subject to determination and the combined current-sample mass spectra 215 only using the spectra of the m/z values of the combined characteristic ions, in the case where the combined known-sample mass spectrum data 130 includes the m/z values of the combined characteristic ions.

The output unit 50 is a mechanism for displaying information to be output by the content determination assistance system 1 to the user, and is, for example, a liquid crystal display, or an organic light-emitting display. Alternatively, instead of or in addition to the above-described mechanism, the output unit 50 is a mechanism for printing the information to be output by the content determination assistance system 1 to the user, and is, for example, a printer.

The input unit 70 is a portion for receiving an operational input to the content determination assistance system 1 by the user, and is, for example, a keyboard, a mouse, a touch pad or a touch panel, or the other pointing device.

Next, an example of process contents of the content determination assistance system of the present embodiment will be described using FIGS. 3 to 9.

<Preparation of Characteristic Mass Spectrum Data and Combined Known-Sample Mass Spectrum Data>

In the content determination assistance system 1 of the present embodiment, prior to assisting the determination as to whether the known compound is contained in the current sample, the characteristic mass spectrum data 110 and the combined known-sample mass spectrum data 130 are prepared.

The characteristic mass spectrum data 110 and the combined known-sample mass spectrum data 130 are prepared in the following process flow, for example.

The standard sample of the known compound is subjected to the pyrolysis GC/MS analysis, and the known-compound mass spectrum data 100 which is the time series data of the mass spectra at predetermined time intervals as illustrated in FIG. 4A is acquired. The plurality of characteristic mass spectra 113 which are characteristic mass spectra are specified among the mass spectra included in the known-compound mass spectrum data 100, the mass spectra being obtained by pyrolyzing the known compound, and the characteristic RIs 115 which are information obtained by indexing, by a predetermined method, the times when the respective characteristic mass spectra 113 are detected are acquired.

Then, the characteristic ions included in each of the characteristic mass spectra 113 (for example, 113a, 113b, and 113c) are selected.

The characteristic mass spectrum data 110 of the known compound is created based on the characteristic mass spectra 113, and the characteristic RI 115 and the values of the selected characteristic ions of each of the characteristic mass spectra 113, which are thus obtained.

Additionally, the characteristic mass spectra 113 obtained as described above are combined for each of ions of the same m/z value to acquire the combined known-sample mass spectra 131, as illustrated in FIG. 4B. However, the characteristic mass spectra 113 are combined after actual ion intensities in each characteristic mass spectrum 113 are reflected and normalized.

Next, the combined characteristic ions are specified from the combined known-sample mass spectra 131. In the present embodiment, as illustrated in FIG. 4B, the ions of the m/z values of 51, 78, 91, 104, 117, 130, 194, 207 and 312 are specified as the combined characteristic ions of the known compound. However, the combined characteristic ions do not always specify the same as the characteristic ions of the characteristic mass spectra 113 (113a to 113c).

The combined known-sample mass spectrum data 130 of the known compound is created based on the combined known-sample mass spectra 131, and the information 133 indicating the name of the known sample corresponding to each combined known-sample mass spectrum 131, and the m/z values of the combined characteristic ions.

Such processes are performed for each known compound capable of being subject to determination whether to be contained in the current sample. The characteristic mass spectrum data 110 of the known compound obtained as a result of the processes is stored in the characteristic mass spectrum DB 11, and the combined known-sample mass spectrum data 130 of the known compound obtained as a result of the processes is stored in the combined known-sample mass spectrum DB 13. Thus, the preparation of the characteristic mass spectrum data 110 and the combined known-sample mass spectrum data 130 is completed.

The content determination assistance system 1 performs the following series of processes of assisting the user in determining whether the known compound is contained in the current sample in a state in which the above-described preparation is completed. The content determination assistance system 1 starts the following, series of processes when the input unit 70 receives a user's operation of starting the determination as to whether the known compound is contained in the current sample.

<First Acquisition Process>

First, the content determination assistance system 1 performs a first acquisition process (FIG. 3/S100). When the process is started, the first acquisition unit 31 acquires the current-sample mass spectrum data 200 which is the information including the time series data of the mass spectra of the current sample at predetermined time intervals, the time series data being collected in the same manner as the known-compound mass spectrum data 100, and the information obtained by indexing times when the respective mass spectra are detected, by the predetermined method, and the acquired current-sample mass spectrum data 200 is stored in the recording unit 10 as necessary, and thus the process is completed.

<Recognition Process>

The recognition unit 32 starts a recognition process (FIG. 3/S200) automatically when the first acquisition process is completed, for example. For example, the recognition unit 32 receives a user's input of the information for specifying the known compound subject to determination, and recognizes the known compound subject to determination based on the input information, and thus the process is completed.

However, when there is no user's input of the information for specifying the known compound subject to determination or the recognition unit 32 is not configured to receive the user's input of the information for specifying the known compound subject to determination, the recognition unit 32 is configured to recognize, as the known compounds subject to determination, all of the known compounds whose characteristic mass spectrum data 110 and combined known-sample mass spectrum data 130 are recorded in the recording unit 10, for example.

Then, the content determination assistance system 1 repeats the following series of processes (FIG. 3/L1) for each of the recognized known compounds subject to determination.

<Second Acquisition Process>

The second acquisition unit 33 starts a second acquisition process (FIG. 3/S300) automatically when the recognition process is completed, for example. When the process is started, the second acquisition unit 33 acquires, from the recording unit 10, the m/z values of the respective characteristic ions and the characteristic RI 115, for each of the characteristic mass spectra 113 relating to the known compound subject to determination which is to be subjected to the current process, and thus the process is completed.

In the description below, the description is made on a case where the number of characteristic mass spectra 113 of the known compound subject to determination which is to be subjected to the current process is three, and the characteristic mass spectra 113 include a first characteristic mass spectrum 113*a*, a second characteristic mass spectrum 113*b*, and a third characteristic mass spectrum 113*c*.

The second acquisition unit 33 acquires the m/z values of the characteristic ions and the characteristic RI 115 in each characteristic mass spectrum 113 of the known compound subject to determination.

In the present embodiment, as illustrated in FIG. 4A, in the first characteristic mass spectrum 113*a*, the m/z values of the characteristic ions are 51, 78, 103, and 104 and the RI is 898. In the second characteristic mass spectrum 113*b*, the m/z values of the characteristic ions are 91, 104, 130, 193, and 208 and the RI is 1749. In the third characteristic mass spectrum 113*c*, the m/z values of the characteristic ions are 91, 117, 194, 207, and 312 and the RI is 2488. The second acquisition unit 33 acquires these values, and thus the process is completed.

<Extraction Process>

The extraction unit 35 starts an extraction process (FIG. 3/S400) automatically when the second acquisition process is completed, for example. When the process is started, the extraction unit 35 extracts, from the current-sample mass spectrum data 200, a plurality of corresponding current-sample mass spectra 201 which are mass spectra detected in predetermined periods including RIs corresponding to characteristic RIs 115, respectively, based on the characteristic RIs 115 acquired by the second acquisition unit 33, and thus the process is completed.

The predetermined period is a period within a fixed value (for example, ±50, ±10% or the like) before and after each RI acquired by the second acquisition unit 33, for example.

That is, if ±50 of each RI is defined as the predetermined period, for example, the predetermined period of the RI corresponding to the first characteristic mass spectrum 113*a* is a period from 848 to 948, the predetermined period of the RI corresponding to the second characteristic mass spectrum 113*b* is a period from 1699 to 1799, and the predetermined period of the RI corresponding to the third characteristic mass spectrum 113*c* is a period from 2438 to 2538.

In the present embodiment, as the corresponding current-sample mass spectra 201 in a period of RI from 848 to 948, the mass spectra including a corresponding current-sample mass spectrum 201*a* at the RI of 894 and a corresponding current-sample mass spectrum 201*b* at the RI of 910 are extracted as the corresponding current-sample mass spectra 201, as illustrated in FIG. 6.

<Detection Process>

The detection unit 37 starts a detection process (FIG. 3/S500) automatically when the extraction process is completed, for example. When the process is started, the detection unit 37 firstly acquires the corresponding current-sample mass spectra 201 extracted from the extraction unit 35 (FIG. 5/S510).

The detection unit 37 repeats processes from S512 to S522 (FIG. 5/L2) for each of the predetermined periods.

Next, the detection unit 37 recognizes the m/z values of the characteristic ions in the characteristic mass spectrum 113 corresponding to the corresponding current-sample mass spectrum 201 which is to be subjected to the current process (FIG. 5/S512) among the characteristic mass spectra 113 acquired by the second acquisition unit 33, and calculates the ion intensities in the mass spectra forming the peaks included in the mass chromatogram in the case where the mass chromatogram is drawn based on the mass spectra extracting the spectra of the recognized m/z values of the characteristic ions among the spectra included in the corresponding current-sample mass spectrum 201 which is to be subjected to the current process (FIG. 5/S514).

In this embodiment, when the characteristic mass spectrum 113 corresponding to the corresponding current-sample mass spectrum 201 which is to be subjected to the current process is the first characteristic mass spectrum 113*a*, the detection unit 37 recognizes that the m/z values of the characteristic ions in the first characteristic mass spectrum 113*a* are 51, 78, 103, and 104. Then, the detection unit 37 calculates the ion intensities in the mass spectra forming the peaks included in the mass chromatogram in the case where the mass chromatogram is drawn based on the mass spectra extracting the spectra of the m/z values of 51, 78, 103, and 104 among the spectra included in the corresponding current-sample mass spectrum 201 which is to be subjected to the current process.

Thereafter, the detection unit 37 detects the high intensity mass spectrum 214 which is the corresponding current-sample mass spectrum 201 in which the ion intensities calculated as described above are higher by a predetermined degree, and the similarity to the characteristic mass spectrum 113 corresponding to the corresponding current-sample mass spectrum 201 is higher by a predetermined degree (FIG. 5/S516).

Here, the detection unit 37 determines whether the ion intensities calculated as described above are higher by a predetermined degree, and determines whether the similarity to the characteristic mass spectrum 113 corresponding to the corresponding current-sample mass spectrum 201 is higher by a predetermined degree. Various methods may be adopted for the above-described determination by the detection unit 37. First, an example of a method of determining whether the ion intensities calculated as described above are higher by a predetermined degree will be described.

An upper chart in FIG. 7A shows a mass chromatogram drawn based on the mass spectra extracting the spectra of the m/z values of the characteristic ions, and represents a state in which two peaks are included. As shown in the upper chart in FIG. 7A, each peak is formed by the plurality of mass spectra.

In such a case, for example, the detection unit 37 determines whether the ion intensities calculated as described above are higher by a predetermined degree according to whether the ion intensity in the mass spectrum forming an apex of the peak at any one m/z value among the mass spectra forming each peak is equal to or higher than a predetermined value. In this case, the mass spectra forming the peak which include the mass spectra determined that the ion intensities are equal to or higher than the predetermined value are subjected to the determination as to whether the similarity to the characteristic mass spectrum 113 is higher by a predetermined degree. Alternatively, the detection unit 37 may be further configured to select the mass spectra determined that the ion intensities are equal to or higher than the ion intensity in percentage (for example, 80%, or the like) in the mass spectrum forming the apex of the peak among the mass spectra forming the peak which include the mass spectra determined that the ion intensities are equal to or higher than the predetermined value, so that only the selected mass spectra are subjected to the determination as to whether the similarity to the characteristic mass spectrum 113 is higher by the predetermined degree.

Alternatively, for example, the detection unit 37 may be configured to determine whether the ion intensities in the mass spectra forming the peak are higher by the predetermined degree according to whether a peak area at any one m/z value of each peak is equal to or greater than a predetermined value. In this case, the mass spectra forming the peak determined that the peak area is equal to or greater than the predetermined value are subjected to the determination as to whether the similarity to the characteristic mass spectrum 113 is higher by the predetermined degree.

In the present embodiment, as shown in FIG. 7A, the detection unit 37 selects, as the mass spectra to be subjected to the determination as to whether the similarity to the characteristic mass spectrum 113 is higher by the predetermined degree, the mass spectra in which the mass spectrum at the RI of 898 is included at the peak forming the apex and the mass spectra in which the mass spectrum at the RI of 910 is included at the peak forming the apex, from the mass chromatogram drawn based on the mass spectra extracting the spectra of the m/z values (51, 78, 103, and 104) of the characteristic ions, in the corresponding current-sample mass spectrum 201 detected in the period of RI from 848 to 948, which is a predetermined period, the corresponding current-sample mass spectrum 201 being subjected to the current process.

Furthermore, the detection unit 37 acquires an integrated mass spectrum 213 for each peak obtained by adding the selected mass spectra for each peak as the preparation for calculating the similarity between the mass spectra selected as described above and the characteristic mass spectrum 113, for example. However, the mass spectra are added after actual ion intensities in each mass spectrum are reflected and normalized.

In the present embodiment, the two peaks are present. Therefore, the mass spectra included at each peak on one side are added to acquire the integrated mass spectrum 213a shown on the lower left side of FIG. 7A, and the mass spectra included at each peak on the other side are added to acquire the integrated mass spectrum 213b shown on the right side of FIG. 7A. Additionally, the detection unit 37 retains the information (203a, 203b) indicating the RI of the mass spectrum totaling the apexes of the peaks in the corresponding integrated mass spectrum 213. In the present embodiment, for subsequent processes, the integrated mass spectra 213 (213a, 213b) each show a state in which only the spectra of the m/z values of the characteristic ions are extracted.

In FIG. 7A, for convenience of description, a mass chromatogram 210 is drawn using the mass spectra when the spectra of the m/z values of the characteristic ions are extracted. However, in the above-described processes, the mass chromatogram does not need to be drawn.

Subsequently, an example of a method in which the detection unit 37 determines whether the similarity to the characteristic mass spectrum 113 corresponding to the corresponding current-sample mass spectrum 201 is higher by the predetermined degree will be described. For example, the detection unit 37 is configured to acquire, from the characteristic mass spectrum DB 11, the characteristic mass spectrum 113 which is to be subjected to the calculation of the similarity to the corresponding integrated mass spectrum 213 to calculate the similarity based on the information indicating the RI of the mass spectrum forming the apexes of the peaks in the corresponding integrated mass spectrum 213, and perform the above-described determination according to whether the similarity is equal to or greater than a predetermined value.

Then, the detection unit 37 detects, as the high intensity mass spectrum 214, the corresponding integrated mass spectrum 213 in which the similarity to the corresponding characteristic mass spectrum 113 is equal to or greater than the predetermined value.

The detection unit 37 determines whether the number of mass spectra detected with respect to one characteristic mass spectrum 113 is two or more. When the number of detected mass spectra is two or more (FIG. 5/S518: Yes), the detection unit 37 detects, as the high intensity mass spectrum 214, the integrated mass spectrum 213 having the highest similarity to the corresponding characteristic mass spectrum 113 (FIG. 5/S520).

When the number of detected mass spectra is one (FIG. 5/S518: No), the detection unit 37 detects the detected mass spectrum as the high intensity mass spectrum 214 (FIG. 5/S522).

Various methods may be adopted as a method in which the detection unit 37 acquires the similarity. However, in the present embodiment, the detection unit 37 calculates the similarity as follows, for example.

The description is made on a case were the number of integrated mass spectra 213 is two, and the characteristic mass spectrum 113 corresponding to these integrated mass spectra 213 is the above-described first characteristic mass spectrum 113a.

In this case, the detection unit 37 recognizes that the number of m/z values used for calculating the similarity is four, namely 51, 78, 103, and 104. Firstly, the detection unit 37 calculates, as the similarity between the first characteristic mass spectrum 113a and one integrated mass spectrum 213a, a value obtained by squaring cos θ of angle formed by two four-dimensional vectors whose coordinates are values representing, in a percentage, the ion intensities at the respective m/z values, the two vectors being used for representing the first characteristic mass spectrum 113a and one integrated mass spectrum 213a.

That is, for example, the detection unit 37 represents the vector of the first characteristic mass spectrum 113a by the following expression (1).

[Expression 1]

$$\vec{A1} \quad (1)$$

Additionally, the detection unit 37 represents the vector of the one integrated mass spectrum 213a by the following expression (2).

[Expression 2]

$$\vec{A2} \quad (2)$$

Then, the detection unit 37 obtains a similarity between the first characteristic mass spectrum 113a and the one integrated mass spectrum 213a by the following expression (3).

[Expression 3]

$$M = \left( \frac{\vec{A1} \cdot \vec{A2}}{|A1||A2|} \right)^2 \quad (3)$$

Where, M represents the similarity.

Subsequently, the detection unit 37 also calculates a similarity between the first characteristic mass spectrum 113a and the other integrated mass spectrum 213b in the same manner.

Thereafter, the detection unit 37 determines which of the integrated mass spectra 213 has the highest similarity by indicating which of the similarity between the first characteristic mass spectrum 113a and the one integrated mass spectrum 213a and the similarity 218b between the first characteristic mass spectrum 113a and the other integrated mass spectrum 213b is higher.

In the case where the two mass spectra completely coincide with each other as a calculation result of the similarity using the above-described calculation method, the similarity is 100% when the similarity is represented in a percentage, for example. Therefore, the integrated mass spectrum 213 in which the similarity closer to 100% is calculated is determined as the integrated mass spectrum 213 having the highest similarity to the first characteristic mass spectrum 113a. In the present embodiment, as illustrated in FIG. 7B, the similarity between the first characteristic mass spectrum 113a and the one integrated mass spectrum 213a is 99%, and the similarity between the first characteristic mass spectrum 113a and the other integrated mass spectrum 213b is 49%. Therefore, the one integrated mass spectrum 213a is detected as the high intensity mass spectrum 214.

For example, the detection unit 37 may calculate the similarity by calculating cos θ of angle formed by the vector of the characteristic mass spectrum 113 and the vector of each integrated mass spectrum 213.

Alternatively, the detection unit 37 may obtain the similarity by calculating the similarity between an approximation curve obtained by using a value representing, in a percentage, the ion intensity of each peak of the characteristic mass spectrum 113 and an approximation curve obtained by using a value representing, in a percentage, the ion intensity of each peak of each integrated mass spectrum 213.

Then, the detection unit 37 exits the loop of L2 when the above-described detection of the high intensity mass spectra 214 is completed for all of the predetermined periods, and thus the process is completed.

<Third Acquisition Process>

The third acquisition unit 39 starts a third acquisition process (FIG. 3/S600) automatically when the detection process is completed, for example. When the process is started, the third acquisition unit 39 combines, for each of ions of the same m/z value, the high intensity mass spectra 214 (214a, 214c, and 214d) which are detected by the detection unit 37 in the respective predetermined periods, as illustrated in FIG. 8, and acquires the combined mass spectra as the combined current-sample mass spectra 215, and thus the process is completed.

FIG. 8 shows that the combined current-sample mass spectrum 215 is acquired by combining the high intensity mass spectrum 214a which is detected in the period of RI from 848 to 948, and the high intensity mass spectrum 214c which is detected in the period of RI from 1699 to 1799, and the high intensity mass spectrum 214d which is detected in the period of RI from 2438 to 2538.

However, the high intensity mass spectra 214 are combined after actual ion intensities in each high intensity mass spectrum 214 are reflected and normalized.

<Concordance Degree Output Process>

The concordance degree output unit 41 starts a concordance degree output process (FIG. 3/S700) automatically when the third acquisition process is completed, for example. When the process is started, the concordance degree output unit 41 outputs a degree of concordance 220 between the combined known-sample mass spectrum 131 relating to the known compound subject to determination and the combined current-sample mass spectrum 215 acquired by the third acquisition unit 39, as illustrated in FIG. 9, and thus the process is completed.

That is, the concordance degree output unit 41 acquires the combined known-sample mass spectrum 131 relating to the known compound subject to determination, the m/z values of the combined characteristic ions, and the information 133 indicating a name of the known sample corresponding to the combined known-sample mass spectrum 131, from the combined known-sample mass spectrum DB 13 with reference to the recording unit 10.

Then, the concordance degree output unit 41 outputs, to the output unit 50, the degree of concordance 220 between the acquired combined known-sample mass spectrum 131 and the combined current-sample mass spectrum 215 acquired by the third acquisition unit 39 in the third acquisition process.

For example, as illustrated in FIG. 9, the concordance degree output unit 41 outputs, to the output unit 50, the combined known-sample mass spectrum 131, the m/z values of the combined characteristic ions, and the information 133 indicating a name of the known sample corresponding to the combined known-sample mass spectrum 131, and the combined current-sample mass spectrum 215, together with the degree of concordance 220. In the present embodiment, the combined known-sample mass spectrum 131 and the combined current-sample mass spectrum 215 each show a state in which only the spectra of the m/z values of the combined characteristic ions are extracted.

Various methods may be adopted as a method of calculating the degree of concordance. However, in the present embodiment, the concordance degree output unit 41 calculates the degree of concordance as follows, for example.

That is, for example, when the number of m/z values of the acquired combined characteristic ions is nine, firstly, the concordance degree output unit 41 calculates, as the degree of concordance between the combined known-sample mass spectrum 131 and the combined current-sample mass spectrum 215, the value obtained by squaring cos θ of angle formed by two nine-dimensional vectors whose coordinates are values representing, in a percentage, the ion intensities at the respective m/z values, the two vectors being used for representing the combined known-sample mass spectrum 131 and the combined current-sample mass spectrum 215.

In this case, for example, the concordance degree output unit 41 represents the combined known-sample mass spectrum 131 by the following expression (4).

[Expression 4]

$$\vec{B1} \quad (4)$$

Additionally, the concordance degree output unit 41 represents the combined current-sample mass spectrum 215 by the following expression (5).

[Expression 5]

$$\vec{B2} \quad (5)$$

Then, the concordance degree output unit 41 obtains the degree of concordance between the combined known-sample mass spectrum 131 and the combined current-sample mass spectrum 215 by the following expression (6).

[Expression 6]

$$N = \left( \frac{\vec{B1} \cdot \vec{B2}}{|B1||B2|} \right)^2 \quad (6)$$

Where N represents the degree of concordance.

The concordance degree output unit 41 outputs the degree of concordance between the combined known-sample mass spectrum 131 and the combined current-sample mass spectrum 215 which is thus calculated, along with the information 133 indicating a name of the known sample corresponding to the combined known-sample mass spectrum 131 by displaying or printing them via the output unit 50, and thus the process is completed.

Alternatively, the concordance degree output unit 41 may calculate the degree of concordance by calculating as follows instead of the above-described expression (6).

That is, for example, the concordance degree output unit 41 represents an average value of the values representing, in a percentage, the ion intensities at the respective m/z values of the combined characteristic ions, relating to the combined known-sample mass spectrum 131, by the following expression (7).

[Expression 7]

$$\overline{Ri} \quad (7)$$

Then, the concordance degree output unit 41 represents an average value of the values representing, in a percentage, the ion intensities at the respective m/z values of the combined characteristic ions, relating to the combined current-sample mass spectrum 215, by the following expression (8).

[Expression 8]

$$\overline{Rj} \quad (8)$$

Then, the concordance degree output unit 41 obtains the degree of concordance between the combined known-sample mass spectrum 131 and the combined current-sample mass spectrum 215 by the following expression (9).

[Expression 9]

$$N2 = \frac{\sum u \in U(Ru, i - \overline{Ri})(Ru, j - \overline{Rj})}{\sqrt{\sum u \in U(Ru, i - \overline{Ri})^2} \sqrt{\sum u \in U(Ru, j - \overline{Rj})^2}} \quad (9)$$

Where U represents a set having, as an element u, the values representing, in a percentage, the ion intensities at the respective m/z values of the combined characteristic ions, relating to the combined known-sample mass spectrum 131 and the combined current-sample mass spectrum 215. Ru, i represents a value representing, in a percentage, the ion intensity at each m/z value of the combined characteristic ions, relating to the combined known-sample mass spectrum 131. Ru, j represents a value representing, in a percentage, the ion intensity at each m/z value of the combined characteristic ions, relating to the combined current-sample mass spectrum 215. N2 represents the degree of concordance.

Alternatively, for example, the concordance degree output unit 41 may be configured to learn, by machine learning in advance, the importance in calculating the degree of concordance of the ion intensity at each value used for calculating the degree of concordance, and weight the value of the ion intensity at each m/z value while reflecting the importance to calculate the degree of concordance.

The above is a series of processes of assisting the user in determining whether the known compound is contained in the sample.

As described above, according to the present invention, the high intensity mass spectrum can be selectively extracted from the corresponding current-sample mass spectra by focusing not on the total ion intensity but on individual characteristic ions of the known compound subject to determination, thereby enhancing the reliability with which the high intensity mass spectrum having high similarity to the characteristic mass spectrum indicating the presence of each characteristic pyrolyzate obtained by pyrolyzing the compound subject to determination is detected in each of the predetermined periods, even when a variety of compounds other than the compounds subject to determination whether to be contained in the current sample are contained as contaminants.

Additionally, a level of possibility that the compound subject to determination is contained in the current sample is output as the degree of concordance. Therefore, the user can be intuitively informed the level of possibility that the known compound subject to determination is contained in the current sample, which makes it possible to effectively assist the user in determining whether the compound subject to determination is contained in the current sample.

In this way, the content determination assistance system of the present invention can effectively assist the user in determining whether the known compound is contained in the sample even when a variety of compounds other than the compounds subject to determination whether to be contained in the sample are contained as contaminants.

Although the embodiment of the present invention has been described above, the present invention is not limited thereto. Various modifications may be made without departing from the scope of the present invention.

For example, the first acquisition unit 31 may acquire the current-sample mass spectrum data 200 via an external storage medium such as a USB memory or a CD-ROM.

Alternatively, for example, the content determination assistance system 1 and the gas chromatograph mass spectrometer 3 may be comprised of the same computer. In this case, the first acquisition unit 31 acquires the current sample mass spectrum data 200 from the storage device of the same computer.

Alternatively, for example, the concordance degree output unit 41 may be configured to output, as the degree of concordance, arithmetic mean or geometric mean of the similarities between the high intensity mass spectra 214 detected by the detection unit 37 in the respective predetermined periods and the characteristic mass spectra corresponding to the respective high intensity mass spectra 214. In this case, the combined known-sample mass spectrum DB 13 and the third acquisition unit 39 are not provided.

Alternatively, for example, when the number of combined known-sample mass spectra 131 in which the degree of concordance to the combined current-sample mass spectrum 215 is higher by a predetermined degree is two or more, the concordance degree output unit 41 may be configured to output, to the output unit 50, the information 133 indicating a name of the known compound corresponding to each of the plurality of combined known-sample mass spectra 131 and the degree of concordance 220 to each of the plurality of combined known-sample mass spectra 131 in a list format.

Alternatively, for example, the detection unit 37 may be configured to obtain the similarity by the same method as the method described as the method in which the concordance degree output unit 41 calculates the degree of concordance, or the concordance degree output unit 41 may be configured to obtain the degree of concordance by the same method as the method described as the method in which the detection unit 37 calculates the similarity.

Alternatively, for example, a configuration in which the detection unit 37 acquires the integrated mass spectra 213 in the detection process, and detects, as the high intensity mass spectrum 214, the integrated mass spectrum 213 having the highest similarity to the characteristic mass spectrum 113 has been described above, but is not limited to thereto.

That is, for example, the detection unit 37 may be configured to acquire the corresponding current-sample mass spectrum 201 in which the ion intensities in the mass spectra forming peaks included in a mass chromatogram are higher by a predetermined degree, in the case where the mass chromatogram is drawn based on the mass spectra extracting the spectra of the m/z values of the characteristic ions acquired by the second acquisition unit 33 among the spectra included in each corresponding current-sample mass spectrum 201, and to detect, as the high intensity mass spectrum 214, the corresponding current-sample mass spectrum 201 having the highest similarity to the characteristic mass spectrum 113 corresponding to the corresponding current-sample mass spectrum 201 in each of the predetermined periods.

Alternatively, the recording unit 10 may record, as the characteristic mass spectrum, the integrated characteristic mass spectrum obtained by adding the mass spectra forming peaks included in a mass chromatogram in the case where the mass chromatogram is drawn based on the characteristic mass spectra of the standard sample, among the mass spectra included in the known-compound mass spectrum data.

REFERENCE SIGNS LIST

1 . . . Content determination assistance system
10 . . . Recording unit
11 . . . Characteristic mass spectrum DB
13 . . . Combined known-sample mass spectrum DB
30 . . . Control unit
31 . . . First acquisition unit
32 . . . Recognition unit
33 . . . Second acquisition unit
35 . . . Extraction unit
37 . . . Detection unit
39 . . . Third acquisition unit
41 . . . Concordance degree output unit

The invention claimed is:

1. A content determination assistance system which assists a user in determining whether a known compound is contained in a current sample, the content determination assistance system comprising:

a recording unit configured to record, for each known compound, characteristic mass spectrum data which is information including a plurality of characteristic mass spectra which are characteristic mass spectra of a standard sample among mass spectra included in known-compound mass spectrum data which is time series data of the mass spectra at predetermined time intervals, the mass spectra being detected by pyrolysis Gas Chromatography/Mass Spectrometry (GC/MS) analysis of the standard sample of the known compound, a characteristic retention time (RT) which is a time when each of the characteristic mass spectra is detected or a characteristic retention index (RI) obtained by indexing the time by a predetermined method, and mass-to-charge ratio (m/z) values of characteristic ions included in each of the characteristic mass spectra;

a first acquisition unit configured to acquire current-sample mass spectrum data which is information including the time series data of the mass spectra of the current sample at the predetermined time intervals, the time series data of the mass spectra of the current sample being collected in a same manner as the known-compound mass spectrum data, and information obtained by indexing times when respective mass spectra are detected or by indexing the times by the predetermined method;

a recognition unit configured to recognize the known compound subject to determination based on information for specifying the known compound subject to determination, the known compound subject to determination being subjected to determination whether to be contained in the current sample;

a second acquisition unit configured to acquire, from the recording unit, the m/z values of respective characteristic ions and the characteristic RT or the characteristic RI, for each of the characteristic mass spectra relating to the recognized known compound subject to determination;

an extraction unit configured to extract, from the current-sample mass spectrum data, a plurality of corresponding current-sample mass spectra which are mass spectra detected in predetermined periods including RTs corresponding to the characteristic RTs or RIs corresponding to the characteristic RIs, respectively, based on the characteristic RTs or the characteristic RIs acquired by the second acquisition unit;

a detection unit configured to detect, from the plurality of corresponding current-sample mass spectra extracted by the extraction unit, a high intensity mass spectrum in each of the predetermined periods, the high intensity mass spectrum being a corresponding current-sample mass spectrum in which ion intensity in the mass spectra forming a peak included in a mass chromatogram is higher by a predetermined degree, in a case where the mass chromatogram is drawn based on the mass spectra extracting the mass spectra of the m/z values of the respective characteristic ions acquired by the second acquisition unit among the mass spectra included in each corresponding current-sample mass spectrum, and a similarity to the characteristic mass spectrum corresponding to the corresponding current-sample mass spectrum is higher by a predetermined degree; and a concordance degree output unit configured to output a degree of concordance between the mass spectra of the known compound subject to determination and the mass spectra of the current sample using the plurality of characteristic mass spectra relating to the known compound subject to determination and the high-intensity mass spectra detected by the detection unit in the respective predetermined periods.

2. The content determination assistance system according to claim 1, wherein the recording unit records, for each known compound, combined known-sample mass spectrum data which is information including combined known-sample mass spectra which are the mass spectra obtained by combining, for each of the characteristic ions of a same m/z value, the plurality of characteristic mass spectra, a third acquisition unit configured to acquire combined current-sample mass spectra which are the mass spectra obtained by combining, for each of the characteristic ions of the same m/z value, the high intensity mass spectra detected by the detection unit in the respective predetermined periods, and the concordance degree output unit is configured to output, as the degree of concordance, the degree of concordance between the combined known-sample mass spectra relating to the known compound subject to determination and the combined current-sample mass spectra.

3. The content determination assistance system according to claim 2, wherein the detection unit acquires the similarity only using the spectra of the m/z values of the characteristic ions.

4. The content determination assistance system according to claim 2, wherein

The combined known-sample mass spectrum data includes the m/z values of combined characteristic ions which are the characteristic ions included in the combined known-sample mass spectrum, and the concordance degree output unit acquires and outputs the degree of concordance only using the mass spectra of the m/z values of the combined characteristic ions.

5. A content determination assistance method of assisting a user in determining whether a known compound is contained in a current sample, the content determination assistance method being executed by a computer comprising: a recording unit configured to record, for each known compound, characteristic mass spectrum data which is information including a plurality of characteristic mass spectra which are characteristic mass spectra of a standard sample among mass spectra included in known-compound mass spectrum data which is time series data of the mass spectra at predetermined time intervals, the mass spectra being detected by a pyrolysis Gas Chromatography/Mass Spectrometry (GC/MS) analysis of the standard sample of the known compound, a characteristic retention time (RT) which is a time when each of the characteristic mass spectra is detected or a characteristic retention index (RI) obtained by indexing the time by a predetermined method, and mass-to-charge ratio (m/z) values of characteristic ions included in each of the characteristic mass spectra, the content determination assistance method comprising:

a first acquisition process of acquiring current-sample mass spectrum data which is information including the time series data of the mass spectra of the current sample at the predetermined time intervals, the time series data of the mass spectra of the current sample being collected in a same manner as the known-compound mass spectrum data, and information obtained by indexing times when respective mass spectra are detected or by indexing the times by the predetermined method;

a recognition process of recognizing the known compound subject to determination based on information for specifying the known compound subject to determination, the known compound subject to determination being subjected to determination whether to be contained in the current sample;

a second acquisition process of acquiring, from the recording unit, the m/z values of respective characteristic ions and the characteristic RT or the characteristic RI, for each of the characteristic mass spectra relating to the recognized known compound subject to determination;

an extraction process of extracting, from the current-sample mass spectrum data, a plurality of corresponding current-sample mass spectra which are mass spectra detected in predetermined periods including RTs corresponding to the characteristic RTs or RIs corresponding to the characteristic RIs, respectively, based on the characteristic RTs or the characteristic RIs acquired by the second acquisition process;

a detection process of detecting, from the plurality of corresponding current-sample mass spectra extracted by the extraction process, a high intensity mass spectrum in each of the predetermined periods, the high intensity mass spectrum being a corresponding current-sample mass spectrum in which ion intensity in the mass spectra forming a peak included in a mass chromatogram is higher by a predetermined degree, in a case where the mass chromatogram is drawn based on the mass spectra extracting the mass spectra of the m/z values of the respective characteristic ions acquired by the second acquisition process among the mass spectra included in each corresponding current-sample mass spectrum, and a similarity to the characteristic mass spectrum corresponding to the corresponding current-sample mass spectrum is higher by a predetermined degree; and a concordance degree output process of outputting a degree of concordance between the mass spectra of the known compound subject to determination and the mass spectra of the current sample using the plurality of characteristic mass spectra relating to the known compound subject to determination and the high-intensity mass spectra detected by the detection process in the respective predetermined periods.

* * * * *